United States Patent
Hajdenberg

(10) Patent No.: US 9,881,485 B2
(45) Date of Patent: Jan. 30, 2018

(54) DEVICE BASED HYGIENE REMINDER, ALARM, AND REPORTING SYSTEM

(71) Applicant: Julio Hajdenberg, Maitland, FL (US)

(72) Inventor: Julio Hajdenberg, Maitland, FL (US)

(*) Notice: Subject to any disclaimer, the term of this patent is extended or adjusted under 35 U.S.C. 154(b) by 7 days.

(21) Appl. No.: 15/073,039

(22) Filed: Mar. 17, 2016

(65) Prior Publication Data

US 2016/0275779 A1    Sep. 22, 2016

Related U.S. Application Data

(60) Provisional application No. 62/134,460, filed on Mar. 17, 2015.

(51) Int. Cl.
| | |
|---|---|
| G08B 21/24 | (2006.01) |
| G08B 25/08 | (2006.01) |
| G08B 5/36 | (2006.01) |
| G06F 19/00 | (2011.01) |
| G08B 21/02 | (2006.01) |
| G09B 19/00 | (2006.01) |
| G08B 21/18 | (2006.01) |

(52) U.S. Cl.
CPC .......... *G08B 21/245* (2013.01); *G08B 25/08* (2013.01); *G06F 19/325* (2013.01); *G06F 19/327* (2013.01); *G08B 5/36* (2013.01); *G08B 21/02* (2013.01); *G08B 21/18* (2013.01); *G09B 19/0076* (2013.01)

(58) Field of Classification Search
CPC ...... G08B 21/02; G08B 21/18; G08B 21/245; G08B 5/36; G06F 19/327; G06F 19/325; G06F 19/0076
See application file for complete search history.

(56) References Cited

U.S. PATENT DOCUMENTS

| | | | |
|---|---|---|---|
| 6,975,231 B2 | 12/2005 | Lane et al. | |
| 7,271,728 B2 | 9/2007 | Taylor et al. | |
| 7,372,367 B2 | 5/2008 | Lane et al. | |
| 7,375,640 B1 | 5/2008 | Plost | |
| 7,477,154 B2 * | 1/2009 | Braunstein | G06Q 10/06 235/377 |
| 7,605,704 B2 | 10/2009 | Munro et al. | |
| 7,755,494 B2 | 7/2010 | Melker et al. | |
| 7,770,782 B2 | 8/2010 | Sahud | |
| 7,804,409 B2 | 9/2010 | Munro et al. | |

(Continued)

*Primary Examiner* — Benyam Haile
(74) *Attorney, Agent, or Firm* — Akerman LLP; Mammen (Roy) P. Zachariah, Jr.

(57) ABSTRACT

A system for providing device-based hygiene reminders, alarms, and reporting is disclosed. In particular, the system may utilize a mobile device capable of wirelessly communicating with a peripheral wearable reader. Prior to a user entering an area, the system may include prompting the user to scan a first tag using the wearable reader. A signal may be sent to the mobile device that alerts the user to perform a hygiene-related action prior to entering the area. At the time of performing the hygiene-related action, the system may require the reader to scan a second tag in proximity to a device associated with the hygiene-related action to disable the alert. After the scanning the second tag, the user may be allowed to enter the area. Information related to the performance of the hygiene-related action may be tracked and utilized to generate reports for assessing compliance with hygiene protocols.

20 Claims, 4 Drawing Sheets

(56) References Cited

U.S. PATENT DOCUMENTS

| | | |
|---|---|---|
| 7,825,812 B2 | 11/2010 | Ogrin et al. |
| 7,855,651 B2 | 12/2010 | Leblond et al. |
| 7,898,407 B2 | 3/2011 | Hufton et al. |
| 7,978,083 B2 | 7/2011 | Melker et al. |
| 8,090,155 B2 | 1/2012 | Lacey et al. |
| 8,169,325 B2 | 5/2012 | Verdiramo et al. |
| 8,237,558 B2 | 8/2012 | Seyed et al. |
| 8,294,584 B2 | 10/2012 | Plost |
| 8,350,706 B2 | 1/2013 | Wegelin et al. |
| 8,395,515 B2 * | 3/2013 | Tokhtuev ............... G06Q 10/00 340/539.13 |
| 8,400,309 B2 * | 3/2013 | Glenn .................. G08B 21/245 134/56 R |
| 8,427,323 B2 | 4/2013 | Alper et al. |
| 8,448,848 B2 | 5/2013 | Sahud et al. |
| 8,474,083 B2 | 7/2013 | Reiter et al. |
| 8,502,680 B2 | 8/2013 | Tokhtuev et al. |
| 8,525,666 B2 | 9/2013 | Melker et al. |
| 8,558,701 B2 | 10/2013 | Wegelin et al. |
| 8,587,437 B2 | 11/2013 | Kyle |
| 8,648,724 B2 | 2/2014 | Forsberg et al. |
| 8,698,637 B2 | 4/2014 | Raichman |
| 8,717,177 B2 | 5/2014 | Cartner |
| 8,823,525 B2 | 9/2014 | Cartner et al. |
| 8,872,665 B2 | 10/2014 | Snodgrass |
| 8,963,721 B2 | 2/2015 | Harris et al. |
| 8,988,228 B2 | 3/2015 | Iseri et al. |
| 8,994,537 B2 | 3/2015 | Pokrajac et al. |
| 9,000,926 B2 | 4/2015 | Hollock et al. |
| 9,000,930 B2 | 4/2015 | Pelland et al. |
| 9,011,607 B2 | 4/2015 | De Luca et al. |
| 9,031,812 B2 * | 5/2015 | Roberts ............... G08B 21/182 235/105 |
| 9,047,755 B2 | 6/2015 | Bonner |
| 9,076,044 B2 | 7/2015 | Dryer et al. |
| 9,117,361 B1 | 8/2015 | Hennigan et al. |
| 9,123,257 B2 | 9/2015 | Vicente |
| 9,131,811 B2 | 9/2015 | Wegelin et al. |
| 9,135,805 B2 | 9/2015 | Freedman et al. |
| 9,143,843 B2 | 9/2015 | De Luca et al. |
| 9,147,334 B2 | 9/2015 | Long et al. |
| 2014/0266692 A1 * | 9/2014 | Freedman ............ G08B 21/245 340/539.11 |

* cited by examiner

DEVICE BASED HYGIENE REMINDER, ALARM, AND REPORTING SYSTEM

CROSS REFERENCE TO RELATED APPLICATIONS AND PRIORITY

The present application claims priority to and the benefit of U.S. Provisional Application No. 62/134,460, filed Mar. 17, 2015, the entirety of which is hereby incorporated by reference.

FIELD OF THE INVENTION

The present application relates to hygiene-based technologies, mobile device technologies, communications technologies, monitoring technologies, and network technologies, and more particularly, to a device-based hygiene reminder, alarm, and reporting system and method.

BACKGROUND

In today's society, there are various environments in which regular hygienic practices are strongly encouraged, if not required. For example, such environments may include, but are not limited to, healthcare environments, food service environments, nursing home environments, daycare environments, bathroom environments, social environments, any other environment, or any combination thereof. In a medical environment, having effective an effective hygienic practice in place is important in preventing or minimizing the spread of diseases and contaminants. Currently, such practices include, but are not limited to, disinfecting reusable medical equipment, ensuring safe disposal of medical waste, requiring medical personnel to wear protective clothing (e.g. face masks, scrubs, glasses, gloves, etc.), sterilizing medical instruments, requiring individuals to wash their hands and/or body, quarantining certain individuals, other practices, or any combination thereof. In food service environments, workers are often required or encouraged to wash their hands, utilize hair nets, utilize gloves, wear face masks, ensure cleanliness of food preparation areas and equipment, ensure safe disposal of food waste, ensure safe handling of food, participate in other similar practices, or a combination thereof. In bathroom environments and social environments, other hygienic practices are utilized to also ensure cleanliness and prevent the spread of diseases and contaminants.

While current hygiene-related practices are often helpful in reducing the spread of various diseases and contaminants, there is still room for substantial improvement. For example, while medical professionals are typically required to wash their hands before performing a surgical operation or other medical procedure, there is often no way of confirming that a particular medical professional washed their hands for the recommended period of time or even washed his or her hands at all. As another example, food service employees are typically required to wash their hands, wear a hair net, and use gloves prior to touching any food items or machinery, however, with current technologies, it is difficult to ensure that such practices are actually being performed. Unhygienic practices or hygienic practices that are not adhered to can lead to patients being susceptible to bacterial and viral infections, patients being ineffectively treated, food customers being inflicted with food poisoning, unsanitary areas, increased costs, or a myriad of other undesired consequences. As a result, hygiene-related technologies may be enhanced and supplemented so as to provide improved hygiene, prevent the spread of communicable diseases and pathogens, provide improved functionality and features, provide greater hygiene standards, and provide substantial cost savings.

SUMMARY

A system and accompanying methods for providing device-based hygiene reminders, alarms, and reporting are disclosed. The system and methods may enable users to utilize devices, such as smartphones, in conjunction with monitoring technologies to alert, monitor, and study hygiene behavior of individuals that are in environments where communicable diseases may be transmitted by contact or other means. In particular, the system and methods may include utilizing a phone-paired reader that interacts with radio frequency identification (RFID) and/or near-field communication (NFC)-tagged doorways, wash stations, soap dispensers, or other similar areas or devices to ensure that users are adhering to hygiene-related practices. The system and methods may also communicate information obtained from such interactions to servers that may analyze the information and provide meaningful reports on the users' hygiene. By doing so, the system and methods may assist in reducing the spread of communicable diseases, reducing the likelihood of spreading contaminants, increasing cleanliness, increasing compliance with hygiene-related practices, reducing instances of food poisoning, along with providing a myriad of other benefits.

In order to accomplish the foregoing, the system and methods may include having a user utilize a mobile device, such as a smartphone, that is capable of wirelessly communicating with a peripheral wearable RFID/NFC reader (i.e. scanner). In certain embodiments, the reader may be included within a bracelet, badge, wand, or other wearable device and may be worn by the user. Before entering a critical area, such as an operating room or food preparation area, the user may be prompted to scan an entry tag using the reader. A signal may be sent to the reader and/or the mobile device to alert the user to perform a hygiene-related action, such as, but not limited to, washing hands, using soap, brushing teeth, showering, any other hygiene-related action, or any combination thereof. The wearable reader may have the ability to generate a visible or audible alert to the user, which may indicate the need for performing the hygiene-related action. Additionally, the mobile device may include sonic, vibratory, and/or light alarm capabilities, which may also be utilized to alert the user to perform the hygiene-related action.

While performing the hygiene-related action or at any other desired time, the reader may need to scan another tag, such as a tag positioned next to a washing station, to shut off or remove the alert. The user may then be prompted to scan another tag to enter the area, or, in certain embodiments, may simply enter the area after performing the hygiene-related action. The mobile device may include a software application that may track all scanning performed by the reader, all interactions between the mobile device, the reader, and the tags, user information, and any other information. The tracked information may be sent to a central computer or server for report preparation and analysis. The prepared reports may indicate which users are effectively performing hygiene-related actions, which critical areas are lacking in hygiene-related compliance, which areas are frequented by the most users, which tags are scanned most often and least often, any other information, or any combination thereof. As a result, the system and methods provide a novel way for increasing hygiene compliance, increasing the cleanliness of critical areas, and reducing the occurrence of unsanitary conditions.

In one embodiment, a system for providing device-based hygiene reminders, alarms, and reporting is disclosed. The system may include a memory that stores instructions and a processor that executes the instructions to perform various operations of the system. The system may perform an operation that includes receiving, on a mobile device of a user, a prompt to scan a first tag for entering an area. After receiving the prompt and by utilizing a radio frequency reader, the system may perform an operation that includes scanning the first tag. The radio frequency reader may be communicatively linked with the mobile device. The system may proceed to perform an operation that includes receiving, on the mobile device and after scanning the first tag, a first alert indicating that a hygiene-related action needs to be performed prior to entering the area. If a second tag in proximity to a first device associated with performing the hygiene-related action is scanned by the radio frequency reader, the system may perform an operation that includes removing the first alert. Moreover, if the second tag is scanned by the radio frequency reader, the system may perform an operation that includes receiving a first signal indicating that the area may be entered.

In another embodiment, a method for providing device-based hygiene reminders, alarms, and reporting is disclosed. The method may include utilizing a memory that stores instructions, and a processor that executes the instructions to perform the various functions of the method. The method may include receiving, on a mobile device of a user, a prompt to scan a first tag for entering an area. After receiving the prompt and by utilizing a radio frequency reader, the method may include scanning the first tag. Notably, the radio frequency reader may be communicatively linked with the mobile device. Additionally, the method may include receiving, on the mobile device and after scanning the first tag, a first alert indicating that a hygiene-related action needs to be performed prior to entering the area. Furthermore, the method may include removing the first alert if a second tag in proximity to a first device associated with performing the hygiene-related action is scanned by the radio frequency reader. Moreover, the method may include receiving, if the second tag is scanned by the radio frequency reader, a first signal indicating that the area may be entered.

According to yet another embodiment, a computer-readable device having instructions for providing device-based hygiene reminders, alarms, and reporting is provided. The computer instructions, which when loaded and executed by a processor, may cause the processor to perform operations including: receiving, on a mobile device of a user, a prompt to scan a first tag for entering an area; scanning, after receiving the prompt and by utilizing a radio frequency reader, the first tag, wherein the radio frequency reader is communicatively linked with the mobile device; receiving, on the mobile device and after scanning the first tag, a first alert indicating that a hygiene-related action needs to be performed prior to entering the area; removing the first alert if a second tag in proximity to a first device associated with performing the hygiene-related action is scanned by the radio frequency reader; and receiving, if the second tag is scanned by the radio frequency reader, a first signal indicating that the area may be entered.

These and other features of the systems, apparatuses, and methods for providing device-based hygiene reminders, alarms, and reporting are described in the following detailed description, drawings, and appended claims.

DETAILED DESCRIPTION OF THE INVENTION

Figure 1:
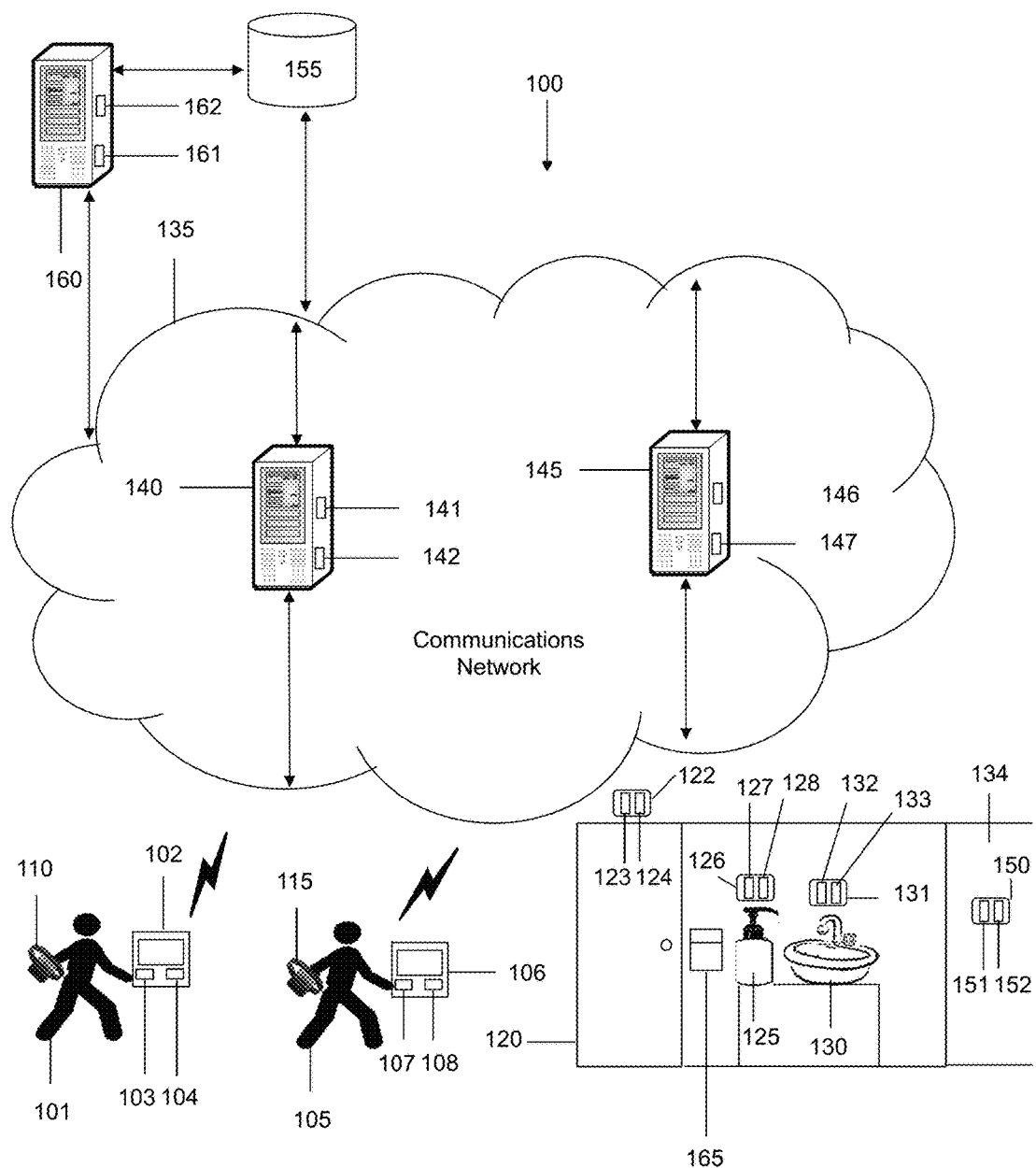
FIG. 1 is a schematic diagram of a system for providing device-based hygiene reminders, alarms, and reporting according to an embodiment of the present disclosure.

A system 100 and accompanying methods for providing device-based hygiene reminders, alarms, and reporting are disclosed. The system 100 and methods may enable users to utilize devices, such as smartphones, in conjunction with monitoring technologies to alert, monitor, and study hygiene behavior of individuals that are in environments where communicable diseases, contaminants, or unhygienic materials may be transmitted by contact or other means. In particular, the system 100 and methods may include utilizing a phone-paired reader that interacts with radio frequency identification (RFID) and/or near-field communication (NFC)-tagged doorways 120, 134, wash stations 130, dispensers 125, or other similar areas or devices to ensure that users are adhering to hygiene-related practices. The system 100 and methods may also communicate information obtained from such interactions to servers that may analyze the information and provide meaningful reports on the users' hygiene. By doing so, the system 100 and methods may assist in reducing the spread of communicable diseases, reducing the likelihood of spreading contaminants, increasing cleanliness, increasing compliance with hygiene-related practices, reducing instances of food poisoning, along with providing a myriad of other benefits.

In order to accomplish the foregoing, the system 100 and methods may include having a user (e.g. first user 101) utilize a mobile device, such as a smartphone, that is capable of wirelessly communicating with a peripheral wearable RFID/NFC reader 110, 115 (i.e. scanner). In certain embodiments, the reader 110, 115 may be included within a bracelet, badge, wand, or other wearable device and may be worn by the user. Before entering a critical area, such as an operating room or food preparation area, the user may be prompted to scan an entry tag 122 using the reader 110, 115. A signal may be sent to the reader 110 and/or the mobile device to alert the user to perform a hygiene-related action, such as, but not limited to, washing hands, using soap, brushing teeth, showering, any other hygiene-related action, or any combination thereof. The wearable reader 110 may have the ability to generate a visible or audible alert to the user, which may indicate the need for performing the hygiene-related action. Additionally, the mobile device may include sonic, vibratory, and/or light alarm capabilities, which may also be utilized to alert the user to perform the hygiene-related action.

While performing the hygiene-related action or at any other desired time, the reader 110 may need to scan another tag, such as a tag positioned next to a washing station 130, to shut off or remove the alert. The user may then be prompted to scan a further tag to enter the area, or, in certain embodiments, may simply enter the area after performing the hygiene-related action. The mobile device may include a software application that may track all scanning performed by the reader, all interactions between the mobile device, the reader, and the tags, user information, and any other information. The tracked information may be sent to central computers or servers 140, 145 for report preparation and analysis. The prepared reports may indicate which users are effectively performing hygiene-related actions, which areas are lacking in hygiene-related compliance, which areas are frequented by the most users, which tags are scanned most often and least often, any other information, or any combination thereof. As a result, the system 100 and methods provide a novel way for increasing hygiene compliance, increasing the cleanliness of critical areas, and reducing the occurrence of unsanitary conditions.

Figure 2:
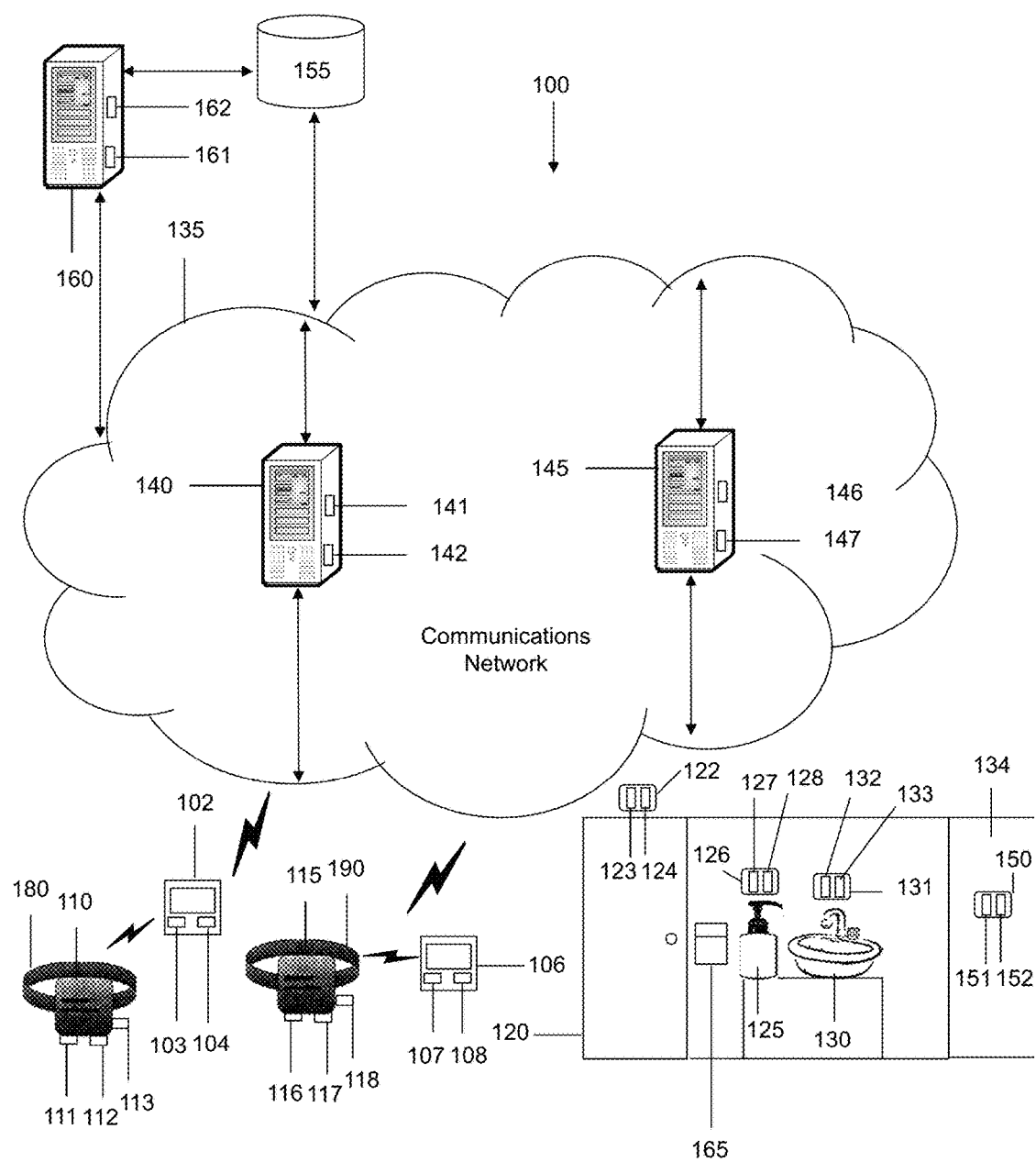
FIG. 2 is a schematic diagram illustrating additional detail, components, and functionality of the system of FIG. 1.

As shown in FIGS. 1-2, a system 100 for providing device-based hygiene reminders, alarms, and reporting is disclosed. In a preferred embodiment, the functionality and features of the system 100 may be supported by utilizing cloud-computing resources and networks. The system 100 may be configured to support, but is not limited to supporting, healthcare services, food preparation services, daycare services, nursing home services, hygiene-related services, telephone services, cloud computing services, RFID-related technologies, NFC-related technologies, short-rage wireless technologies, content delivery services, information delivery services, network services, voice-over-internet protocol services (VoIP), voice-over-long-term-evolution (VoLTE) services, LTE services, software as a service (SaaS) applications, software applications and services, productivity applications and services, mobile applications and services, any other computing applications and services, or any combination thereof. The system may include a first user 101 that may utilize a first user device 102 to access data, access content, access services, make telephone calls, and/or to perform a variety of other functions. As an example, the first user 101 may utilize first user device 102 to request information and data from one or more servers, upload data and information to one or more servers, connect to a call with a second user 105 using a second user device 106, perform any other operations, or any combination thereof.

In certain embodiments, the first user 101 may be a physician, a nurse, a food services worker, a caretaker, or any other individual that regularly accesses areas in which hygiene is an important concern. The first user device 102 may be equipped for mobile communication and may also be configured to include componentry for communicating with NFC devices, RFID devices, short-range wireless device, and/or other types of wireless devices. The first user device 102 may include a memory 103 that includes instructions, and a processor 104 that executes the instructions from the memory 103 to perform the various operations that are performed by the first user device 102. In certain embodiments, the processor 104 may be hardware, software, or a combination thereof. In certain embodiments, the first user device 102 may be a computer, a laptop, a tablet device, a phablet, a server, a mobile device, a smartphone, a smart watch, or any other type of computing device. Illustratively, the first user 101 may be a physician and the first user device 102 is shown as a smartphone device in FIGS. 1-2. In certain embodiments, the first user device 102 may communicate with any of the devices in the system 100, or any combination thereof, by utilizing infrared radiation, radio frequency technologies, Bluetooth connectivity technologies (e.g. Bluetooth Low Energy, etc.), ZigBee, Z-Wave, any type of wireless protocol, radio technologies, or any combination thereof. For example, the first user device 102 may include and/or be connected to a Bluetooth module or other short-range wireless communications module. The first user device 102 may communicate with the devices and components of the system 100 via one or more network connections. In certain embodiments, the first user device 102 may include any number of microphones, speakers, lights, or other componentry.

The system 100 may also include a second user 105 that may utilize a second user device 106 to also access data, access content, access services, make telephone calls, and/or to perform a variety of other functions. In certain embodiments, the second user 105 may be a physician, a nurse, a food services worker, a caretaker, or any other individual that regularly accesses areas for which hygiene is an important concern. Much like the first user device 102, the second user device 106 may be equipped for mobile communication and may also be configured to include componentry for communicating with NFC devices, RFID devices, short-range wireless device, and/or other types of wireless devices. In certain embodiments, the second user device 106 may be utilized by the second user 105 to communicate with the first user 101 via a call connected to the first user device 102. The second user 105 may download and/or upload data and information by utilizing the second user device 106. The second user device 106 may include a memory 107 that includes instructions, and a processor 108 that executes the instructions from the memory 107 to perform the various operations that are performed by the second user device 106. In certain embodiments, the processor 108 may be hardware, software, or a combination thereof. Similar to the first user device 102, in certain embodiments, the second user device 106 may be a computer, a laptop, a tablet device, a phablet, a server, a mobile device, a smartphone, a smart watch, or any other type of computing device. Illustratively, the second user 105 may be a food services worker (or another physician) and the second user device 106 is shown as a mobile device in FIG. 1. In certain embodiments, the second user device 106 may communicate with any of the devices in the system 100, or any combination thereof, by utilizing infrared radiation, radio frequency technologies, Bluetooth connectivity technologies, ZigBee, Z-Wave, any type of wireless protocol, radio technologies, or any combination thereof. In certain embodiments, the second user device 106 may include any number of microphones, speakers, lights, or other componentry.

In certain embodiments, the first and second user devices 102, 106 may have any number of software applications and/or application services stored and/or accessible thereon. For example, the first and second user devices 102, 106 may include applications that generate alerts, healthcare applications, hygiene-related applications, food service applications, tracking applications, monitoring applications, daycare-based applications, cloud-based applications, VoIP applications, other types of phone-based applications, media streaming applications, content-based applications, media-editing applications, database applications, gaming applications, internet-based applications, browser applications, mobile applications, service-based applications, productivity applications, video applications, music applications, social media applications, any other type of applications, any types of application services, or a combination thereof.

In certain embodiments, the software applications and services may include one or more graphical user interfaces so as to enable the first and second users 101, 105 to readily interact with the software applications. The software applications and services may also be utilized by the first and second users 101, 105 to interact with the any device in the system 100, any network in the system 100, or any combination thereof. In certain embodiments, the first and second user devices 102, 106 may include associated telephone numbers, device identities, or any other identifiers to uniquely identify the first and second user devices 102, 106.

In certain embodiments, the first and second user devices 102, 106 may have corresponding device profiles. In certain embodiments, each of the devices, applications, and systems in the system 100 may have its own corresponding device profile. Information included in a device, system, or application profile may include, but is not limited to, information specifically corresponding to the first and second user devices 102, 106, information identifying the types of devices that the first and second user devices 102, 106 are, information relating to how the first user 101 utilizes the first user device 102, information relating to how the second user 105 utilizes the second user device 106, information identifying what type of services, locations, and information the first user 101 and second user 105 are authorized to access, information indicating each type of component included in the first and second user devices 102, 106, information identifying the processing power, storage capacity, download capabilities, and upload capabilities associated with the first and second user devices 102, 106, any other information associated with the first and second user devices 102, 106, or any combination thereof. The device profiles may be made accessible to any device, network, or a combination thereof, in the system 100.

In addition to device profiles, the system 100 may also include user profiles. A user profile may be a profile corresponding to the first user 101, the second user 105, or any other user. For example, the first user's 101 profile may include information, such as, but not limited to, a name of the first user 101, a gender of the first user 101, the age of the first user 101, an occupation of the first user 101, languages spoken by the first user 101, any demographic information associated with the first user 101, information identifying the first user device 102 and the second user device 106, information identifying a location of the first user 101, information identifying the types of applications that the first user 101 utilizes, information identifying the specific locations that the first user 101 is authorized to access, information identifying the first user's 101 hygiene-related activities, information identifying the first user's 101 compliance with hygiene practices and protocols, information identifying the first user's 101 hygiene-related score, any other information, or any combination thereof. The user profiles may also include an image of the first user 101, any other content or information, or any combination thereof. The user profiles may be stored directly on the first user device 102, the second user device 106, the database 155, on any other device in the system 100, or on any combination thereof. Additionally, the user profiles may be accessible by any device in the system 100, any network in the system 100, or a combination thereof.

The system 100 may include one or more readers or scanners, such as first and second readers 110, 115. The first and second readers 110, 115 may be configured to communicate with other devices in the system 100 by utilizing RFID technologies, NFC technologies, any type of short-range or long-range wireless technologies, or any combination thereof. For example, the first and second readers 110, 115 may be RFID readers that may generate radio frequency fields (or energy fields) that may be utilized to activate and communicate with one or more tags, such as first, second, third, and fourth tags 122, 126, 131, 150. The first reader 110 may include any functionality and componentry of a transceiver and may include an antenna 111, which may be utilized to transmit and receive signals to communicate with the tags 122, 126, 131, 150. Additionally, the first reader 110 may include an integrated circuit 112, which may include the functionality of a processor, memory, or a combination thereof, and may be a chip. The integrated circuit 112 may be configured to transmit signals, instructions, data, information, or any combination thereof. The integrated circuit 112 may also be configured to store and process and any information received from the tags 122, 126, 131, 150 or from any other device in the system 100, such as first and second user devices 102, 106. Any information processed and/or stored by the integrated circuit 112 may be transmitted to communications network 135, the first and second user devices 102, 106, or to any other device in the system 100. The first reader 110 may also include a communications module 113, such as a Bluetooth or NFC module, that may be utilized to communicate information to and from the first and second user devices 102, 106, which may also have their own corresponding communications modules. In FIGS. 1-2, the communications module 113 may allow the first reader 110 to be communicatively paired with the first user device 102. Notably, in certain embodiments, the first reader 110 may include any functionality of a traditional RFID reader, NFC reader, other reader, or a combination thereof. Additionally, in certain embodiments, the first reader 110 may include any type of mechanism that may enable the first reader 110 to serve as a wearable device. For example, in FIGS. 1-2, the first reader 110 has a strap 180, which may be configured to allow the first user 101 to wear the first reader 110 on the first user's 101 arm or leg. In certain embodiments, instead of using a strap 180, the first reader 110 may be affixed with Velcro, a clip, or other fastening mechanisms so that the first reader 110 may be easily worn by the first user 101.

Much like the first reader 110, the second reader 115 may include any functionality and componentry of a transceiver and may include an antenna 116, which may be utilized to transmit and receive signals to communicate with the tags 122, 126, 131, 150. Additionally, the second reader 115 may include an integrated circuit 117, which may include the functionality of a processor, memory, or a combination thereof, and may be a chip. The integrated circuit 117 may be configured to transmit signals, instructions, data, information, or any combination thereof. The integrated circuit 117 may also be configured to store and process and any information received from the tags 122, 126, 131, 150 or from any other device in the system 100, such as first and second user devices 102, 106. Any information processed and/or stored by the integrated circuit 117 may be transmitted to communications network 135, the first and second user devices 102, 106, or to any other device in the system 100. The second reader 115 may also include a communications module 118, such as a Bluetooth or NFC module, that may be utilized to communicate information to and from the first and second user devices 102, 106, which may also have their own corresponding communications modules. In FIGS. 1-2 the communications module 118 may allow the second reader 115 to be communicatively paired with the second user device 106. Notably, in certain embodiments, the second reader 115 may include any functionality of a traditional RFID reader, NFC reader, other reader, or a combination thereof. Additionally, in certain embodiments, the second reader 115 may include any type of mechanism that may enable the second reader 115 to be a wearable device. For example, in FIGS. 1-2, the second reader 115 has a strap 190, which may be configured to allow the second user 105 to wear the second reader 115 on the second user's 105 arm or leg. In certain embodiments, instead of using a strap 190, the second reader 115 may be affixed with Velcro, a clip, or other fastening mechanisms so that the first reader 110 may be easily worn by the second user 105, such as on the second user's 105 shirt or pants. In certain embodiments, the second reader 115 may be coupled to the second user device 106 as well.

The system 100 may also include an entry barrier 120, such as a door, that is configured to open and close. In certain embodiments, the entry barrier 120 may be a gate, a lock, any type of entry barrier, or any combination thereof. The entry barrier 120 may be configured to prevent or grant access to one or more areas. Such areas may include, but are not limited to, an operating room, a patient room, a food preparation area, a daycare room, a food service area, a critical area, an area where hygiene is important, any type of area, or any combination thereof. The entry barrier 120 may have a first tag 122 positioned in proximity to the entry barrier 120 or even on a portion of the entry barrier 120 itself. In FIGS. 1-2, the first tag 122 is positioned above the entry barrier 120, which, in FIGS. 1-2, is a door. The first tag 122 may be a RFID tag, an NFC tag, a transceiver, any type of tag capable of wirelessly communicating with the first and second readers 110, 115, or any combination thereof. In certain embodiments, the first tag 122 may include an antenna 123 and an integrated circuit 124, which may be a chip. The antenna 123 may be attached to the integrated circuit 124, and may be configured to absorb signals propagated from either of the first and second readers' 110, 115 antennas 111, 116. The signals may be absorbed by the antenna 123 when the first tag 122 is within range of the radio frequency fields (or other energy fields) generated by the first and second readers 110, 115. The absorbed signals may provide energy to supply power and activate the integrated circuit 124 of the first tag 122.

Once the integrated circuit 124 of the first tag 122 is activated, the first tag 122 may communicate with the readers 110, 115 and transmit any information stored within the first tag 122 to the readers 110, 115, such as by utilizing antenna 123. For example, the information that may be transmitted may be information that identifies the first tag 122 (e.g. an identifier, such as a numeric or string-based identifier), identifies the entry barrier 120, identifies a hygiene-related procedure needed for an area beyond the entry barrier 120, identifies statistics associated with the use of the first tag 122, any other information, or a combination thereof. The integrated circuits 112, 117 of the first and second readers 110, 115 may process the information and transmit the information to the first and/or second user devices 102, 106 and/or to the servers 140, 145 of the communications network 135 for further processing and/or handling. In certain embodiments, when the first tag 122 is scanned by either the first or second reader 110, 115, the system 100 may perform any number of actions. For example, when the first tag 122 is scanned by the first reader 110, information from the first tag 122 may be sent to the first reader 110, which may then be transmitted to an application executing on the first user device 102 and to the servers 140, 145. In an exemplary scenario, the servers 140, 145 may process the information and may transmit an alert to the first user device 102, which may be displayed on a graphical user interface of the application executing on the first user device 102. The alert, for example, may indicate that the first user 101 needs to wash his or her hands or perform some other hygiene-related activity before entering a certain area.

Additionally, the system 100 may also include a dispenser 125, which may be a soap dispenser, antibacterial solution dispenser, a cleansing solution dispenser, or any type of dispenser that may reside within a bathroom, cleaning station, or other cleaning facility. The dispenser 125 may hold any type of substance that may be utilized by users to wash or clean their hands, body parts, clothing, or even devices. The dispenser 125 may have a tag (i.e. second tag 126) positioned in proximity to the dispenser 125 or even on a portion of the dispenser 125 itself. In FIGS. 1-2, the second tag 126 is positioned above the dispenser 125, which, in FIGS. 1-2, is a soap dispenser. Much like the first tag 122, the second tag 126 may be a RFID tag, an NFC tag, a transceiver, any type of tag capable of wirelessly communicating with the first and second readers 110, 115, or any combination thereof. In certain embodiments, the second tag 126 may include an antenna 127 and an integrated circuit 128, which may be a chip. The antenna 127 may be attached to the integrated circuit 128, and may be configured to absorb signals propagated from either of the first and second readers' 110, 115 antennas 111, 116. The signals may be absorbed by the antenna 127 when the second tag 126 is within range of the radio frequency fields (or other energy fields) generated by the first and second readers 110, 115. The absorbed signals may provide energy to supply power and activate the integrated circuit 128 of the second tag 126.

Once the integrated circuit 128 of the second tag 126 is activated, the second tag 126 may communicate with the readers 110, 115 and transmit any information stored within the second tag 126 to the readers 110, 115, such as by utilizing antenna 127. For example, the information that may be transmitted may be information that identifies the second tag 126 (e.g. an identifier, such as a numeric or string-based identifier), identifies the dispenser 125, identifies a hygiene-related procedure needed for an area beyond the location of the dispenser 125, identifies statistics associated with the use of the second tag 126 (e.g. how often the second tag 126 has been scanned), information identifying how much soap or cleaning solution is dispensed from the dispenser 125, any other information, or a combination thereof. The integrated circuits 112, 117 of the first and second readers 110, 115 may process the information and transmit the information to the first and/or second user devices 102, 106 and/or to the servers 140, 145 of the communications network 135 for further processing and/or handling. In certain embodiments, when the second tag 126 is scanned by either the first or second reader 110, 115, the system 100 may perform any number of actions. For example, when the second tag 126 is scanned by the first reader 110, information from the second tag 126 may be sent to the first reader 110, which may then be transmitted to an application executing on the first user device 102 and to the servers 140, 145. In an exemplary scenario, the servers 140, 145 may process the information and may transmit a signal containing information to the first user device 102, which may be displayed on a graphical user interface of the application executing on the first user device 102. The information, for example, may indicate that the first user 101 has utilized the dispenser 125 and that the first user 101 may need to wash his hands next.

Furthermore, the system 100 may also include a washing station 130, which may be any type of washing station that may reside within a bathroom, cleaning station, or other cleaning facility. For example, the washing station may be a sink and faucet combination or a shower. The washing station 130 may be utilized by users to wash or clean their hands, body parts, clothing, or even devices. The washing station 130 may have a tag (i.e. third tag 131) positioned in proximity to the washing station 130 or even on a portion of the washing station 130 itself. In FIGS. 1-2, the third tag 131 is positioned directly above the washing station 130. Much like the first and second tags 122, 126, the third tag 131 may be a RFID tag, an NFC tag, a transceiver, any type of tag capable of wirelessly communicating with the first and second readers 110, 115, or any combination thereof. In certain embodiments, the third tag 131 may include an antenna 132 and an integrated circuit 133, which may be a chip. The antenna 132 may be attached to the integrated circuit 133, and may be configured to absorb signals propagated from either of the first and second readers' 110, 115 antennas 111, 116. The signals may be absorbed by the antenna 132 when the third tag 131 is within range of the radio frequency fields (or other energy fields) generated by the first and second readers 110, 115. The absorbed signals may provide energy to supply power and activate the integrated circuit 133 of the third tag 131.

Once the integrated circuit 133 of the third tag 131 is activated, the third tag 131 may communicate with the readers 110, 115 and transmit any information stored within the third tag 131 to the readers 110, 115, such as by utilizing antenna 132. For example, the information that may be transmitted may be information that identifies the third tag 131 (e.g. an identifier, such as a numeric or string-based identifier), identifies the washing station 130 itself, identifies a hygiene-related procedure needed for an area beyond the location of the washing station 130, identifies statistics associated with the use of the third tag 131 (e.g. how often the third tag 131 has been scanned), information identifying how often and how long the washing station 130 is utilized by users, any other information, or a combination thereof. The integrated circuits 112, 117 of the first and second readers 110, 115 may process the information and transmit the information to the first and/or second user devices 102, 106 and/or to the servers 140, 145 of the communications network 135 for further processing and/or handling. In certain embodiments, when the third tag 131 is scanned by either the first or second reader 110, 115, the system 100 may perform any number of actions. For example, when the third tag 131 is scanned by the first reader 110, information from the third tag 131 may be sent to the first reader 110, which may then be transmitted to an application executing on the first user device 102 and to the servers 140, 145. In an exemplary scenario, the servers 140, 145 may process the information and may transmit a signal containing information to the first user device 102, which may be displayed on a graphical user interface of the application executing on the first user device 102. The information, for example, may indicate that the first user 101 has washed his or her hands and that the first user 101 may enter a particular area.

Moreover, the system 100 may further include another entry barrier 134, which may be much like entry barrier 120. In certain embodiments, the entry barrier 134 may be a gate, a lock, any type of entry barrier, or any combination thereof. The entry barrier 134 may be configured to prevent or grant access to one or more areas. The entry barrier 134 may have a fourth tag 150 positioned in proximity to the entry barrier 134 or even on a portion of the entry barrier 134 itself. In FIGS. 1-2, the fourth tag 150 is positioned on the entry barrier 134, which, in FIGS. 1-2, is a door. The fourth tag 150 may be a RFID tag, an NFC tag, a transceiver, any type of tag capable of wirelessly communicating with the first and second readers 110, 115, or any combination thereof. In certain embodiments, the fourth tag 150 may include an antenna 151 and an integrated circuit 152, which may be a chip. The antenna 151 may be attached to the integrated circuit 152, and may be configured to absorb signals propagated from either of the first and second readers' 110, 115 antennas 111, 116. The signals may be absorbed by the antenna 151 when the fourth tag 150 is within range of the radio frequency fields (or other energy fields) generated by the first and second readers 110, 115. The absorbed signals may provide energy to supply power and activate the integrated circuit 152 of the fourth tag 150.

Once the integrated circuit 152 of the fourth tag 150 is activated, the fourth tag 150 may communicate with the readers 110, 115 and transmit any information stored within the fourth tag 150 to the readers 110, 115, such as by utilizing antenna 151. For example, the information that may be transmitted may be information that identifies the fourth tag 150 (e.g. an identifier, such as a numeric or string-based identifier), identifies the entry barrier 134, identifies statistics associated with the use of the fourth tag 150 (e.g. how often the entry barrier 134 has been opened or closed, any other information, or a combination thereof. The integrated circuits 112, 117 of the first and second readers 110, 115 may process the information and transmit the information to the first and/or second user devices 102, 106 and/or to the servers 140, 145 of the communications network 135 for further processing and/or handling. In certain embodiments, when the fourth tag 150 is scanned by either the first or second reader 110, 115, the system 100 may perform any number of actions. For example, when the fourth tag 150 is scanned by the first reader 110, information from the fourth tag 150 may be sent to the first reader 110, which may then be transmitted to an application executing on the first user device 102 and to the servers 140, 145. In an exemplary scenario, the servers 140, 145 may process the information and may transmit a signal to the first user device 102, which may be displayed on a graphical user interface of the application executing on the first user device 102. The signal, for example, may indicate that the first user 101 may proceed to a certain area now that the fourth tag 150 has been scanned and the first user 101 has performed a hygiene-related action, such as washing his hands.

In certain embodiments, the system 100 may also include an apparatus 165. The apparatus 165 may be any type of device that may be associated with performing a hygiene-related action. For example, the apparatus 165 may be a paper towel dispenser, a hand dryer, a hand cloth dispenser, a glove dispenser, a goggle dispenser, a scrub dispenser, a hair net dispenser, a sterile clothing dispenser, any type of hygiene-related device, or any combination thereof. In certain embodiments, the apparatus 165 may be paired with the second tag 126 or its own separate tag. Much like in the scenarios described above, the second tag 126 or separate tag may store information, which may be transmitted to the first and second readers 110, 115, the servers 140, 145, and/or the first and second user devices 102, 106 For example, the information may indicate information that identifies the second tag 126 (e.g. an identifier, such as a numeric or string-based identifier) or separate tag, identifies the apparatus 165, identifies statistics associated with the use of the second tag 126 or separate tag (e.g. how often the apparatus 165 has been utilized or scanned, any other information, or a combination thereof). In an exemplary scenario, the servers 140, 145 may process the information and may transmit a signal to the first user device 102, which may be displayed on a graphical user interface of the application executing on the first user device 102. The signal, for example, may confirm that the first user 101 has utilized the apparatus 165 and may proceed to perform another hygiene-related action or enter an area, if authorized to do so.

The system 100 may also include a communications network 135. The communications network 135 of the system 100 may be configured to link each of the devices in the system 100 to one another, and may be configured to support the functionality and services of the system 100. For example, the communications network 135 may be utilized by the first user device 102 to connect with other devices within or outside communications network 135, such as servers 140, 145. Additionally, the communications network 135 may be configured to transmit, generate, and receive any information and data traversing the system 100. In certain embodiments, the communications network 135 may include any number of servers, databases, or other componentry, and may be controlled by a service provider. In certain embodiments, the communications network 135 may be subscribed to by the first and second users 101, 105. The communications network 135 may also include and be connected to a radio access network, a cloud-computing network, an IMS network, a VoIP network, a VoLTE network, an LTE network, a wireless network, an Ethernet network, a fiber network, a satellite network, a broadband network, a cellular network, a private network, a cable network, the Internet, an internet protocol network, a MPLS network, a content distribution network, an internet protocol television network, any network, or any combination thereof. Illustratively, servers 140, 145 are shown as being included within communications network 135. In certain embodiments, the communications network 135 may be part of a single autonomous system that is located in a particular geographic region, or be part of multiple autonomous systems that span several geographic regions.

In certain embodiments, the communications network 135 may be configured to deliver data, media content, and service using an internet protocol suite and by utilizing packet switching. The communications network 135 may provide the ability to deliver data and content requested by the first and second users 101, 105, transport data provided by the readers 110, 115, transport data generated by the first and second user devices 102, 106, provide any data generated by any other device of the system 100, or any combination thereof. In certain embodiments, the communications network 135 may include any of the components and functionality found in traditional communication networks. In certain embodiments, the communications network 135 may include hardware components that include any of the functional features of a radio access network. The communications network 135 may be configured to provide cellular services, any type of services, or any combination thereof. The communications network 135 may include any number of antennae, transceivers, digital signal processors, control electronics, GPS receivers, electrical power sources, radio equipment, and electronics equipment to create a cell for the communications network 135. The communications network 135 may be configured to communicate with and receive content and data streams from any other network or system, or any combination thereof.

Notably, the functionality of the system 100 may be supported and executed by using any combination of the servers 140, 145, and 160. In certain embodiments, the server 140 may include a memory 141 that includes instructions, and a processor 142 that executes the instructions from the memory 141 to perform various operations that are performed by the server 140. The processor 142 may be hardware, software, or a combination thereof. Similarly, the server 145 may include a memory 146 that includes instructions, and a processor 147 that executes the instructions from the memory 146 to perform the various operations that are performed by the server 145. In certain embodiments, the servers 140, 145, and 160 may be network servers, routers, gateways, computers, mobile devices or any other suitable computing device. In certain embodiments, the servers 140, 145 may be communicatively linked to the communications network 135, any network, any device in the system 100, or any combination thereof. In certain embodiments, the servers 140, 145 may reside within the communications network 135.

The database 155 of the system 100 may be utilized to store and relay information that traverses the system 100, cache content that traverses the system 100, store data about each of the devices in the system 100 and perform any other typical functions of a database. In certain embodiments, the database 155 may be connected to or reside within the communications network 135, any other network, or a combination thereof. Additionally, the database 155, in certain embodiments, may serve as a data and content source for stored data and content that may be accessed by the communication network 135 so that the communication network 135 may obtain the data and content for the first and second users 101, 105 (or other users) in an efficient and effective manner. In certain embodiments, the database 155 may serve as a central repository for data and content and information requested by the first and second users 101, 105. Furthermore, the database 155 may include a processor and memory or be connected to a processor and memory to perform the various operation associated with the database 155.

In certain embodiments, the database 155 may be connected to servers 140, 145, 160, first user device 102, second user device 106, the readers 110, 115, any other device or system, or any combination thereof. The database 155 may also store information and metadata obtained from the system 100, store media content, store metadata and other information associated with the first and second users 101, 105, store user profiles associated with the first and second users 101, 105, store device profiles associated with the first user device 102, the second user device 106, and/or any other device in the system 100, store location information, store communications traversing the system 100, store information associated with any device or signal in the system 100, store information relating to patterns of usage relating to the first and second user devices 102, 106, store information utilized for identifying communications network 135, store any type of demographic information associated with the first and second users 101, 105, store email account information for the first and second users 101, 105, store any data obtained or transmitted by the readers 110, 115, store any data received or transmitted from the tags 122, 126, 131, 150, store time difference criteria specified by the first and second users 101, 105 or others, store threshold values associated with hygiene-related actions that trigger alerts, store hygiene scores for the first and second users 101, 105, store information identifying the tags 122, 126, 131, 150, store information identifying the readers 110, 115, store reports generated by the system 100, store information identifying how many times a user went into a particular area in comparison to the amount of times that the user performed a hygiene-related action, store any type of alert, store any information traversing the system 100, or any combination thereof. Furthermore, the database 155 may be configured to process queries sent to it by any device in the system 100.

Operatively and referring to FIGS. 1-2, the system 100 may provide for device-based hygiene reminders, alarms, and reporting as shown in the following exemplary scenario. In the example scenario, the first user 101 may be a physician, who may have an operation to perform on a patient in an operating room. Upon arriving in a vicinity of the operating room, the first user 101 may receive a prompt on the first user device 102 to scan an entry tag using a reader 110 worn by the first user 101. The prompt may be delivered to the first user device 102 in response to detecting that the first user device 102 and/or the reader 110 are in proximity to the area, such as by GPS, based on detection of the reader's 110 radio frequency field, or based on other means. The prompt may be visually displayed or audibly outputted on the first user device 102, such as by utilizing an application executing on the first user device 102. The first user 101 may approach the first tag 122 positioned above the entry barrier 120 (i.e. door) so that first tag 122 is within range of the radio frequency fields generated by the reader 110. The first tag 122 may be activated and may transmit information stored on the tag 122 to the reader 100. The information may include information identifying the entry barrier 120, information associated with the operating room, information identifying hygiene-related actions that need to be performed before entering the operating room, any other information, or any combination thereof.

An alert may be sent to the first user device 102 to alert the first user 101 to wash his hands prior to entering the operating room to perform the surgical procedure. The alert may be a visual alert, audible alert, text alert, video alert, a phone call to the first user device 102, any type of alert, or any combination thereof. The first user 101 may be allowed to pass the entry barrier 120 so that the first user 101 may access the dispenser 125, the washing station 130, and/or the apparatus 165. The first user 101 may dispense soap from the dispenser 125 onto his hands and may scan the second tag 126 above the dispenser 125 using the wearable reader 110. Based on the scanning of the second tag 126, the first alert may be disabled or shut off and a second alert may be sent to the first user device 102, which may indicate that the first user 101 needs to wash his hands using the dispensed soap. The first user 101 may then proceed to wash his hands using the soap and then scan the third tag 131 associated with the washing station 131. At this point, the second alert may be shut off and a signal may be sent to the first user device 102 indicating that the first user 101 may enter the operating room. In certain embodiments, the first user 101 may simply enter the operating room and proceed with the performing the operation on the patient if there are no further entry barriers 120, 134 that the first user 101 needs to pass to get to the operating room. However, if there is additional entry barrier 134 to getting to the operating room, the first user 101 may scan the fourth tag 150 to get past the entry barrier 134 and enter the operating room.

All of the information gathered by the reader 110 based on the scanning of the first, second, and third tags 122, 126, 131 may be transmitted and sent to the communications network 135 and/or the first user device 102 for further processing. Additionally, information from the first user's 101 profile may also be sent to the communications network 135. The information gathered from the reader and/or the first user device 102 may be processed by the servers 140, 145 to generate a report for the first user 101. The report may indicate the first user's 101 hygiene score, which may indicate the number of times the user went into a particular area in comparison to the number of times the user actually performed a particular hygiene-related action. Additionally, the report may identify the first user 101, identify ways in which the first user 101 may improve hygiene, and indicate which areas that the first user 101 has accessed or attempted to access. Furthermore, the report may indicate how he compares to other users in the system 100, such as second user 105, who, in this example, may be a nurse or another physician. The reports may be transmitted to the first user device 102 and be accessed by the application executing on the first user device 102. The information in the report may be displayed to the first user 101 via an interface of the first user device 102. Notably, the system 100 may generate reports for each user in the system 100, and may adjust the alerts and types of alerts sent to the users based on their individual reports and hygiene scores.

Notably, as shown in FIGS. 1-2, the system 100 may perform any of the operative functions disclosed herein by utilizing the processing capabilities of server 160, the storage capacity of the database 155 or any other component of the system 100 to perform the operative functions disclosed herein. The server 160 may include one or more processors 162 that may be configured to process any of the various functions of the system 100. The processors 162 may be software, hardware, or a combination of hardware and software. Additionally, the server 160 may also include a memory 161, which stores instructions that the processors 162 may execute to perform various operations of the system 100. For example, the server 160 may assist in processing loads handled by the various devices in the system 100, such as, but not limited to, transmitting prompts to the first and second user devices 102 before they enter an area, 106 to scan a tag for entering an area; scanning a tag by utilizing a reader 110, 115; transmitting or receiving alerts indicating that a hygiene-related action needs to be performed prior to entering an area; determining if the hygiene-related action has been performed; determining if additional tags have been scanned by the reader 110, 115; disabling or removing alerts; transmitting or receiving signals indicating that an area may be entered after performing a hygiene-related action; transmitting information relating to the performance of the hygiene-related action, along with user information to the servers 140, 145; and performing any other suitable operations conducted in the system 100 or otherwise. In one embodiment, multiple servers 160 may be utilized to process the functions of the system 100. The server 160 and other devices in the system 100 may utilize the database 155 for storing data about the devices in the system 100 or any other information that is associated with the system 100. In one embodiment, multiple databases 155 may be utilized to store data in the system 100.

Although FIGS. 1-2 illustrate specific example configurations of the various components of the system 100, the system 100 may include any configuration of the components, which may include using a greater or lesser number of the components. For example, the system 100 is illustratively shown as including a first user device 102, a second user device 106, a first reader 110, a second reader 115, a first tag 122, a second tag 126, a third tag 131, a fourth tag 150, an apparatus 165, a communications network 135, a server 140, a server 145, a database 155, and a server 160. However, the system 100 may include multiple first user devices 102, multiple second user devices 106, multiple first readers 110, multiple second readers 115, multiple first tags 122, multiple second tags 126, multiple third tags 131, multiple fourth tags 150, multiple apparatuses 165, multiple communications networks 135, multiple servers 140, multiple servers 145, multiple databases 155, and multiple servers 160, or any number of any of the other components in the system 100. Furthermore, in certain embodiments, substantial portions of the functionality and operations of the system 100 may be performed by other networks and systems that may be connected to system 100.

Figure 3:
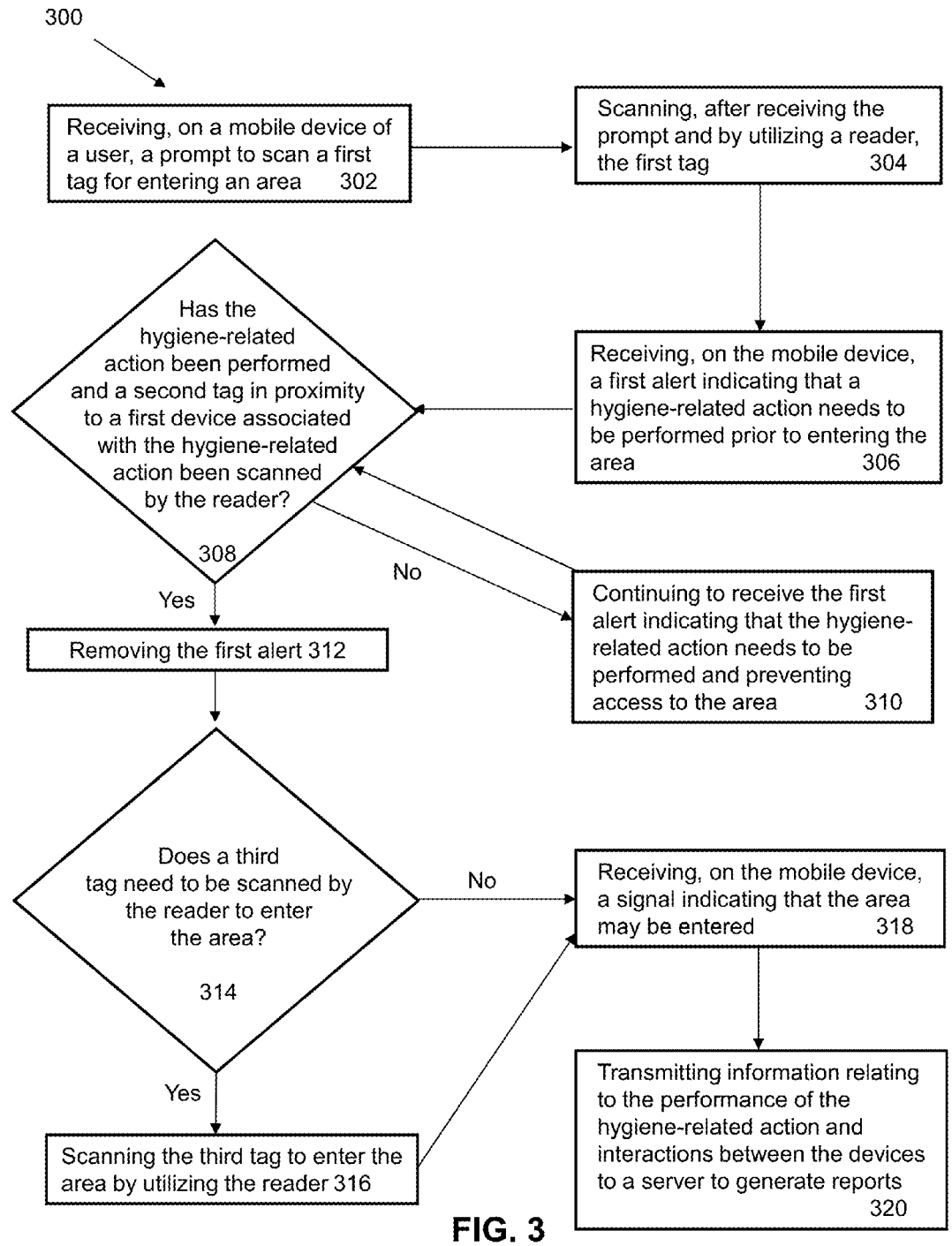
FIG. 3 is a flow diagram illustrating a sample method for providing device-based hygiene reminders, alarms, and reporting according to an embodiment of the present disclosure.

As shown in FIG. 3, an exemplary method 300 for device-based hygiene reminders, alarms, and reporting is schematically illustrated, and may include, at step 302, receiving, on a mobile device of a user, a prompt to scan a first tag for entering an area. For example, the first user 101 may receive a prompt that may be displayed on a graphical user interface of an application executing on the first user device 102. In certain embodiments, the receiving and/or transmitting of the prompt may be performed by utilizing an application executing on the first or second user device 102, 106, the server 140, the server 145, the server 160, the communications network 135, the first and second readers 110, 115, any combination thereof, or by utilizing any other appropriate program, network, system, or device. At step 304, the method 300 may include scanning, after receiving the prompt and by utilizing a reader, the first tag. For example, the first user 101 may utilize the wearable reader 110 to scan the first tag 122 positioned above entry barrier 120. In certain embodiments, the scanning may be performed by utilizing the readers 110, 115, the tags 122, 126, 131, 150, any combination thereof, or by utilizing any other appropriate program, network, system, or device.

At step 306, the method 300 may include receiving, on the mobile device, a first alert indicating that a hygiene-related action needs to be performed prior to entering the area that the user wants to enter. For example, the alert may be transmitted to an application executing on the first user device 102, and the application may display the alert as a visual alert, a text-based alert, a sound-based audible alert, any combination thereof, or any other alert, that indicates that the first user 101 needs to wash his hands before entering the area. In certain embodiments, the application may cause a light (e.g. LED) of the first user device 102 to turn on and/or pulse in a certain manner. In certain embodiments, the receiving or transmitting of the alert may be performed by utilizing the first or second user device 102, 106, the server 140, the server 145, the server 160, the communications network 135, the first and second readers 110, 115, any combination thereof, or by utilizing any other appropriate program, network, system, or device. At step 308, the method 300 may include determining if the hygiene-related action has been performed and if a second tag in proximity to a first device associated with the hygiene-related action has been scanned by the reader. For example, it may be determined that the first user 101 washed his hands if the first user 101 has scanned the tag above a washing station 130. In this particular example, the first device may be the washing station 130 and the second tag may be the tag 131. In certain embodiments, the determining may be performed by utilizing the first or second user device 102, 106, the server 140, the server 145, the server 160, the communications network 135, the first and second readers 110, 115, any combination thereof, or by utilizing any other appropriate program, network, system, or device.

If, at step 308, it is determined that the hygiene-related action has not been performed and the second tag in proximity to the first device associated with the hygiene-related action has not been scanned by the reader, the method 300 may include proceeding to step 310. At step 310, the method 300 may include continuing to receive the first alert indicating the hygiene-related action needs to be performed, and preventing access to the area. For example, using the example above, if the first user 101 has not washed his hands at the washing station 130 and has not scanned tag 131, the alert may continue to be received at the first user device 102 or even the reader 110 worn by the first user 101. In certain embodiments, the alert may be continued to be received by utilizing the first or second user device 102, 106, the server 140, the server 145, the server 160, the communications network 135, the first and second readers 110, 115, any combination thereof, or by utilizing any other appropriate program, network, system, or device. If, however, at step 308, it is determined that the hygiene-related action has been performed and the second tag in proximity to the first device has been scanned by the reader, the method 300 may include, at step 312, removing the first alert. For example, the servers 140, 145 may transmit a signal to cause the alert to no longer be outputted on the first user device 102 or the reader 110. In certain embodiments, the removing of the first alert may be performed by utilizing the first or second user device 102, 106, the server 140, the server 145, the server 160, the communications network 135, the first and second readers 110, 115, any combination thereof, or by utilizing any other appropriate program, network, system, or device.

At step 314, the method 300 may include determining if a third tag needs to be scanned by the reader before the user can enter the area. In certain embodiments, the determining may be performed by utilizing the first or second user device 102, 106, the server 140, the server 145, the server 160, the communications network 135, the first and second readers 110, 115, any combination thereof, or by utilizing any other appropriate program, network, system, or device. If, at step 314, it is determined that a third tag needs to be scanned by the reader before the user can enter the area, the method 300 may include, at step 316, scanning the third tag to enter the area by utilizing the reader. For example, the first user 101 may scan the tag 150 positioned on entry barrier 134 by utilizing the reader 110 worn by the first user 101. In certain embodiments, the scanning may be performed by utilizing the first and second readers 110, 115, the tags 122, 126, 131, 150, any combination thereof, or by utilizing any other appropriate program, network, system, or device. At step 318, the method 300 may include receiving, on the mobile device, a signal indicating that the area may be entered. For example, the first user device 102 may receive a signal from the servers 140, 145 indicating that the first user 101 may enter the area. The first user 101 may proceed to enter the area. The signal may be received by an application executing on the first user device 102 and may be displayed as text content, image content, video content, audio content, or as an alert on the first user device 102. In certain embodiments, the receiving and/or transmitting of the signal may be performed by utilizing the first or second user device 102, 106, the server 140, the server 145, the server 160, the communications network 135, the first and second readers 110, 115, any combination thereof, or by utilizing any other appropriate program, network, system, or device.

If, however, at step 314, it is determined that a third tag does not need to be scanned by the reader to enter the area, the method 300 may include skipping step 316 and proceeding directly to step 318. At this point, the user may enter the area. Once the signal is received at the mobile device at step 318, the method may include transmitting, at step 320, tracked information relating to the performance of the hygiene-related action and information exchanged between the devices in the system 100 to the servers 140, 145 and or mobile device for further processing. For example, any information obtained by the reader from any of the tags may be transmitted to the servers 140, 145 and/or the first user device 102. Additionally, information associated with the user that scanned the tags may also be transmitted. Furthermore, information indicating the times at which the user scanned the tags and information relating to how long the user performed the hygiene-related action may also be transmitted. Once transmitted, the tracked information may be utilized by the servers 140, 145 and/or the mobile device to generate reports including the tracked information. For example, the report may indicate the name of the first user 101, when the first user 101 scanned each of the tags on his way to the area, how long the first user 101 washed his hands, the number of times the first user 101 entered the area versus the number of times the first user 101 washed his hands, any other information, or any combination thereof. In certain embodiments, the information may be transmitted and processed by utilizing the first or second user device 102, 106, the server 140, the server 145, the server 160, the communications network 135, the first and second readers 110, 115, any combination thereof, or by utilizing any other appropriate program, network, system, or device. Notably, the method 300 may further incorporate any of the functionality and features as described for system 100 or as otherwise described herein.

Notably, the system 100 and methods disclosed herein may include additional functionality and features. For example, in certain embodiments, the functionality provided by the system 100 and the method may be performed by utilizing a special-purpose processor specifically configured to perform the functions according to the present disclosure. Additionally, in certain embodiments, the tags 122, 126, 131, 150 may be passive RFID or NFC tags, however, in other embodiments, the tags 122, 126, 131, 150 may be active RFID or NFC tags. If the tags 122, 126, 131, 150 are active RFID or NFC tags, they may include power sources, such as batteries to provide power to the tags 122, 126, 131, 150. Furthermore, in certain embodiments, the users may be allowed to set time difference criteria into the applications executing on the first and second user devices 102, 106. The first user 101 may set the time difference criteria by setting a threshold value in the application that may be utilized to trigger when an alert for performing a hygiene-related action is sent by the system 100 to the first user device 102. As an example, the first user 101 may specify that a threshold amount of time has to occur between hand washing events before an alert is triggered. The first user 101 may specify that if three hours has passed since the last time the first user 101 washed his hands, the first user 101 should receive an alert if the first user is attempting to enter a particular area. The alert may indicate that the first user 101 needs to wash his hands again before entering the area. If the first user 101 washed his hands within two hours of entering the area and the threshold amount of time is three hours, the system 100 may not generate an alert since the first user 101 has washed his hands recently. In certain embodiments, the time difference criteria may be set by the system 100 or may be based on the type of area that the first user 101 is attempting to access.

In certain embodiments, if the first user 101 has previously washed his hands and he washed his hands at a time that indicates that the time difference criteria has not been exceeded, a signal may be sent to the first user device 102 indicating that the user may enter the area without having to perform a hygiene-related action. For example, an LED of the first user device 102 may light green if the first user 101 does not have to perform the hygiene-related action and light red if the first user 101 does have to perform the hygiene-related action. In certain embodiments, the users may be given the option to change the time difference criteria at will via the application executing on the first and second user devices 102, 106. In certain embodiments, each time a tag 122, 126, 131, 150 is scanned, the system 100 may generate a time stamp log indicating when each tag 122, 126, 131, 150 was scanned by the user. The time stamp logs may be utilized by the system 100 to determine if the time difference criteria has been satisfied or not. Additionally, the time stamp logs may be utilized to supplement the reports generated by the system. In certain embodiments, the reports may include hygiene scores for each user. The hygiene score may be determined, for example, based on the number of times the user went into a particular area divided by the number of times the user actually performed a hygiene-related action. The hygiene score may also be based on the amount of times a user has performed a hygiene-related action divided by the number of opportunities the user had to perform the hygiene-related action.

In certain embodiments, if the reports indicate that a particular user washes their hands on a regular or threshold basis before entering a particular area, the system 100 may reduce the frequency of the alerts or even eliminate the alerts entirely if the hygiene score for the user is above a certain threshold. However, if the user's hygiene score starts to slip, the alerts may be restarted and sent again to the mobile device of the user until the user's hygiene score is high enough again. In certain embodiments, the intensity, frequency, and type of alert may be adjusted in real-time based on the user's current hygiene score. For example, if first user 101 has a hygiene score that is below a certain threshold, the alerts outputted by the first user device 102 or the reader 110 may include both audible and visual alerts. However, if the second user 105 has a hygiene score that is above a certain threshold, the system 100 may cause only one type of alert to be outputted, such as the visual alert.

In certain embodiments, the functionality, software, and features of the system 100 may be upgraded by pushing updates from the servers 140, 145 and communications network 135 to the other devices in the system 100. For example, the servers 140, 145 may transmit software updates to the first and second user devices 102, 106 to update the applications executing on the first and second user devices 102 that display the alerts to the first and second users 101, 105. As another example, the servers 140, 145 may push updates to the first and second readers 110, 115 to update the information stored on the integrated circuits 112, 117. As yet another example, the information stored on the tags 122, 126, 131, 150 may also be changed and adjusted as well. In certain embodiments, the formats of the reports and the specific information contained in the reports may be updated by the system 100 through updates. In certain embodiments, the applications on the first and second user devices 102, 106 may be updated by having the first and second user devices 102, 106 access an online store that contains one or more software updates.

In further embodiments, the system 100 is not configured to the specific configuration as illustrated in FIGS. 1-2. For example, any number of tags, readers, or devices may be utilized, and any number of communications networks 135 and servers 140, 145 may be utilized. Additionally, any type of conditions may be specified to trigger the alerts or not trigger the alerts. Furthermore, the components and functionality of the system 100 may be adapted to any type of environment, any types of hygiene standards, any types of users, and any types of devices. In certain embodiments, the system 100 does not have to be limited to monitoring hygiene-related actions, but may be configured to monitor and ensure compliance for any type of activity or action, such as a behavioral activity or action. For example, the system 100 may be utilized to ensure that employees are arriving at work on time, ensure that employees are checking out at the right time from work, ensure that users are eating certain types of foods, ensure that students are studying instead of wasting time doing leisure activities, ensure that patients are following a doctor's prescribed regimen for diet and medicine, ensure that athletes are training according to the regimens that they are supposed to follow, ensure that musicians are practicing their instruments according to schedule, ensure that restaurant workers are following food preparation guidelines, ensure that waiters are serving customers according to guidelines, ensure that any type of activity or action is being performed according to guidelines, or any combination thereof.

Figure 4:
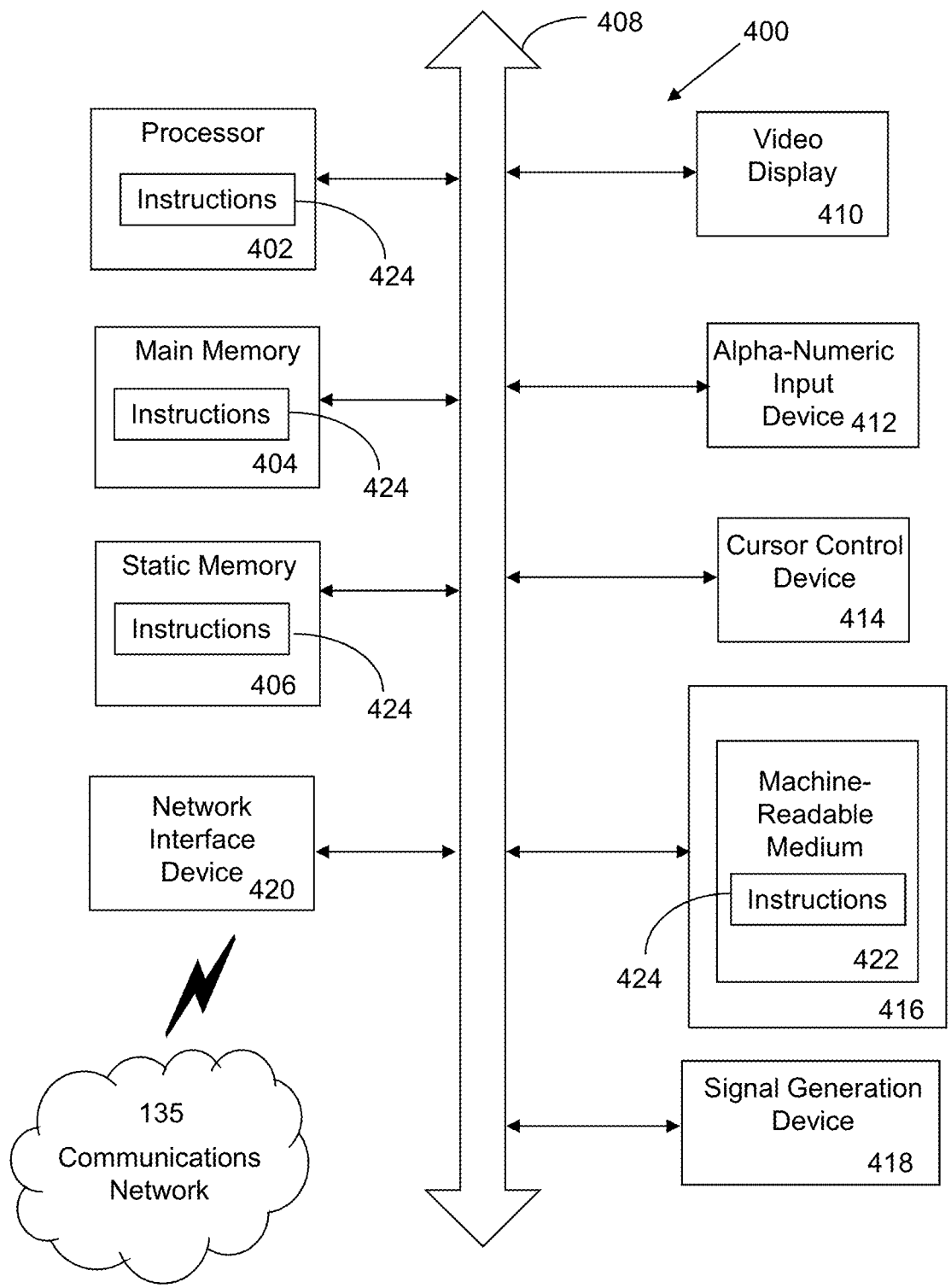
FIG. 4 is a schematic diagram of a machine in the form of a computer system within which a set of instructions, when executed, may cause the machine to perform any one or more of the methodologies or operations of the systems and methods for providing device-based hygiene reminders, alarms, and reporting.

Referring now also to FIG. 4, at least a portion of the methodologies and techniques described with respect to the exemplary embodiments of the system 100 can incorporate a machine, such as, but not limited to, computer system 400, or other computing device within which a set of instructions, when executed, may cause the machine to perform any one or more of the methodologies or functions discussed above. The machine may be configured to facilitate various operations conducted by the system 100. For example, the machine may be configured to, but is not limited to, assist the system 100 by providing processing power to assist with processing loads experienced in the system 100, by providing storage capacity for storing instructions or data traversing the system 100, or by assisting with any other operations conducted by or within the system 100.

In some embodiments, the machine may operate as a standalone device. In some embodiments, the machine may be connected (e.g., using communications network 135, another network, or a combination thereof) to and assist with operations performed by other machines and systems, such as, but not limited to, the first user device 102, the second user device 106, the first reader 110, the second reader 115, the first tag 122, the second tag 126, the third tag 131, the fourth tag 150, the apparatus 165, the server 140, the server 145, the database 155, the server 160, any other device, or any combination thereof. The machine may be connected with any component in the system 100. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 400 may include a processor 402 (e.g., a central processing unit (CPU), a graphics processing unit (GPU, or both), a main memory 404 and a static memory 406, which communicate with each other via a bus 408. The computer system 400 may further include a video display unit 410, which may be, but is not limited to, a liquid crystal display (LCD), a flat panel, a solid state display, or a cathode ray tube (CRT). The computer system 400 may include an input device 412, such as, but not limited to, a keyboard, a cursor control device 414, such as, but not limited to, a mouse, a disk drive unit 416, a signal generation device 418, such as, but not limited to, a speaker or remote control, and a network interface device 420.

The disk drive unit 416 may include a machine-readable medium 422 on which is stored one or more sets of instructions 424, such as, but not limited to, software embodying any one or more of the methodologies or functions described herein, including those methods illustrated above. The instructions 424 may also reside, completely or at least partially, within the main memory 404, the static memory 406, or within the processor 402, or a combination thereof, during execution thereof by the computer system 400. The main memory 404 and the processor 402 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 422 containing instructions 424 so that a device connected to the communications network 135, another network, or a combination thereof, can send or receive voice, video or data, and to communicate over the communications network 135, another network, or a combination thereof, using the instructions. The instructions 424 may further be transmitted or received over the communications network 135, another network, or a combination thereof, via the network interface device 420.

While the machine-readable medium 422 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device, or "computer-readable device" shall accordingly be taken to include, but not be limited to: memory devices, solid-state memories such as a memory card or other package that houses one or more read-only (non-volatile) memories, random access memories, or other rewritable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

I claim:

1. A system, comprising:
a memory that stores instructions; and
a processor that executes the instructions to perform operations, the operations comprising:
receiving, on a mobile device of a user, a prompt to scan a first tag for entering an area;
scanning, after receiving the prompt and by utilizing a radio frequency reader, the first tag, wherein the radio frequency reader is communicatively linked with the mobile device;
receiving, on the mobile device and after scanning the first tag, a first alert indicating that a hygiene-related action needs to be performed prior to entering the area;
removing the first alert if a second tag in proximity to a first device associated with performing the hygiene-related action is scanned by the radio frequency reader;
receiving, if the second tag is scanned by the radio frequency reader, a first signal indicating that the area may be entered; and
preventing access to the area if the second tag is not scanned by the radio frequency reader.

2. The system of claim 1, wherein the operations further comprise determining a first time that a previously completed hygiene-related action was performed by the user.

3. The system of claim 2, wherein the operations further comprise determining a second time corresponding to when the first tag is scanned by the radio frequency reader.

4. The system of claim 3, wherein the operations further comprise determining a difference between the first time and the second time.

5. The system of claim 4, wherein the operations further comprise receiving, on the mobile device, a second signal indicating that the area may be entered without performing the hygiene-related action if the difference between the first time and the second time is less than a threshold value.

6. The system of claim 1, wherein the operations further comprise determining a first amount of time that the user has performed the hygiene-related action.

7. The system of claim 6, wherein the operations further comprise receiving, on the mobile device, a second alert indicating that the hygiene-related action needs to be performed for a longer duration of time if the first amount of time is less than a threshold value.

8. The system of claim 1, wherein the operations further comprise determining if a third tag in proximity to a second device associated with performing the hygiene-related action is scanned by the radio frequency reader.

9. The system of claim 8, wherein the operations further comprise receiving the first signal indicating that the area may be entered only if the third tag in proximity to the second device is scanned before the second tag is scanned.

10. The system of claim 1, wherein the operations further comprise tracking information associated with scanning the first tag and the second tag, and wherein the operations further comprise transmitting the tracked information to a server for processing.

11. The system of claim 1, wherein the operations further comprise scanning, by utilizing the radio frequency reader and after receiving the first signal, a fourth tag to enter the area.

12. The system of claim 1, wherein the operations further comprise determining a hygiene score for the user.

13. A method, comprising:
receiving, on a mobile device of a user, a prompt to scan a first tag for entering an area;
scanning, after receiving the prompt and by utilizing a radio frequency reader, the first tag, wherein the radio frequency reader is communicatively linked with the mobile device;
receiving, on the mobile device and after scanning the first tag, a first alert indicating that a hygiene-related action needs to be performed prior to entering the area;
removing, by utilizing instructions from a memory that are executed by a processor, the first alert if a second tag in proximity to a first device associated with performing the hygiene-related action is scanned by the radio frequency reader;
receiving, if the second tag is scanned by the radio frequency reader, a first signal indicating that the area may be entered; and
preventing access to the area if the second tag is not scanned by the radio frequency reader.

14. The method of claim 13, further comprising displaying the first alert on the mobile device as a visual indicator on an application of the mobile device.

15. The method of claim 13, further comprising outputting the first alert on the mobile device as a sound.

16. The method of claim 13, further comprising tracking information associated with scanning the first tag and the second tag, and wherein the operations further comprise transmitting the tracked information to a server for processing.

17. The method of claim 13, further comprising continuing to receive the first alert if the second tag in proximity to the first device is not scanned by the radio frequency reader.

18. The method of claim 13, further comprising determining a hygiene score for the user.

19. The method of claim 13, further comprising determining a first amount of time that the user has taken to perform the hygiene-related action, and further comprising receiving, on the mobile device, a second alert indicating that the hygiene-related action needs to be performed for a longer duration of time if the first amount of time is less than a threshold value.

20. A non-transitory computer-readable device comprising instructions, which, when loaded and executed by a processor, cause the processor to perform operations, the operations comprising:
- receiving, on a mobile device of a user, a prompt to scan a first tag for entering an area;
- scanning, after receiving the prompt and by utilizing a radio frequency reader, the first tag, wherein the radio frequency reader is communicatively linked with the mobile device;
- receiving, on the mobile device and after scanning the first tag, a first alert indicating that a hygiene-related action needs to be performed prior to entering the area;
- removing the first alert if a second tag in proximity to a first device associated with performing the hygiene-related action is scanned by the radio frequency reader;
- receiving, if the second tag is scanned by the radio frequency reader, a first signal indicating that the area may be entered; and
- preventing access to the area if the second tag is not scanned by the radio frequency reader.

* * * * *